(12) United States Patent
Pestronk

(10) Patent No.: US 7,175,989 B2
(45) Date of Patent: Feb. 13, 2007

(54) ANTIBODIES TO TRISULFATED HEPARIN DISACCHARIDE IN PAINFUL SENSORY AXONAL NEUROPATHY

(76) Inventor: Alan Pestronk, 6 Forrest Ridge Pl., St. Louis, MO (US) 63105

( * ) Notice: Subject to any disclaimer, the term of this patent is extended or adjusted under 35 U.S.C. 154(b) by 475 days.

(21) Appl. No.: 10/225,474

(22) Filed: Aug. 20, 2002

(65) Prior Publication Data

US 2004/0038311 A1    Feb. 26, 2004

(51) Int. Cl.
  *G01N 33/53* (2006.01)
(52) U.S. Cl. .................. 435/7.1; 435/7.92; 435/7.2; 435/329; 436/506; 436/507
(58) Field of Classification Search .............. 435/7.1, 435/7.92, 7.2, 329; 436/506, 507
See application file for complete search history.

(56) References Cited

OTHER PUBLICATIONS

O'Leary, C.P., et al., "The role of antiglycolipid antibodies in peripheral neuropathies", *Curr. Opin. Neurol.*, 13:583-588 (2000).
Quarles, R.H., et al., "Autoantibodies Associated with Peripheral Neuropathy", *Muscle & Nerve*, 22:800-822 (1999).
Pestronk, A., et al., "Serum antibodies to heparan sulfate glycosaminoglycans in Guillain-Barré syndrome and other demyelinating polyneuropathies", *Journal of Neuroimmunology*, 91:204-209 (1998).
Pestronk, A., et al., "Polyneuropathy syndromes associated with serum antibodies to sulfatide and myelin-associated glycoprotein", *Neurology*, 41:357-362 (1991).
Holland, N.R., et al., "Intraepidermal nerve fiber density in patients with painful sensory neuropathy", *Neurology*, 48:708-711 (1997).
Periquet, M.I., et al., "Painful sensory neuropathy—Prospective evaluation using skin biopsy", *Neurology*, 53:1641-1647 (1999).
Kreuger, J., et al., "Sequence Analysis of Heparan Sulfate Epitopes with Graded Affinities for Fibroblast Growth Factors 1 and 2*", *Journal of Biological Chemistry*, 276:30744-30752 (2001).
Guimond, S., et al., "Activating and Inhibitory Heparin Sequences for FGF-2 (Basic FGF)" *Journal of Biological Chemistry*, 268(32):23906-23914 (1993).
Maccarana, M., et al., "Minimal Sequence in Heparin/Heparan Sulfate Required for Binding of Basic Fibroblast Growth Factor*", *Journal of Biological Chemistry*, 268(32):23898-23905 (1993).
Rusnati, M., et al., "Distinct Role of 2-0-, N-, and 6-0-Sulfate Groups of Heparin in the Formation of the Ternary Complex with Basic Fibroblast Growth Factor and Soluble FGF Receoptor-1", *Biochemical and Biophysical Research Communications*, 203(1):450-458 (1994).
Tessler, S., et al., "Heparin Modulates the Interaction of $VEGF_{165}$ with Soluble and Cell Associated flk-1 Receptors*", *Journal of Biological Chemistry*, 269(17):12456-12461 (1994).
Nicole, S., et al., "Perlecan, the major proteoglycan of basement membranes, is altered in patients with Schwartz-Jampel syndrom (chondrodystrophic myotonia)", *Nature Genet.*, 26:480-483 (2000).
Gorson, K.C., et al., "Axonal neuropathy associated with monoclonal gammopathy of undetermined significance", *Journal of Neurology, Neurosurgery, and Psychiatry*, 63:163-168 (1997).
Gorson, K.C., "Clinical Features, Evaluation, and Treatment of Patients with Polyneuropathy Associated with Monoclonal Gammopathy of Undetermined Significance (MGUS)", *Journal of Clinical Apheresis*, 14:149-153 (1999).
Di Troia, A., et al., "Clinical features and anti-neural reactivity in neuropathy associated with IgG monoclonal gammopathy of undetermined significance", *Journal of the Neurological Sciences*, 164:64-71 (1999).

*Primary Examiner*—Long V. Le
*Assistant Examiner*—Jacob Cheu
(74) *Attorney, Agent, or Firm*—Hamilton, Brook, Smith & Reynolds, P.C.

(57) ABSTRACT

Methods aiding in the diagnosis of certain painful, predominantly sensory, polyneuropathies are disclosed, in which the amount of antibodies to trisulfated disaccharide is assessed in a test sample. Also disclosed are kits that can be used in the methods of the invention.

24 Claims, 2 Drawing Sheets

FIGURE 2

ANTIBODIES TO TRISULFATED HEPARIN DISACCHARIDE IN PAINFUL SENSORY AXONAL NEUROPATHY

BACKGROUND OF THE INVENTION

The binding of serum IgM antibodies, including M-proteins, to glycolipids or glycoproteins is associated with several chronic polyneuropathy syndromes (O'Leary, C. P. and Willison, J. J., *Curr. Opin. Neurol.* 13:583–588 (2000); Quarles, R. H. and Weiss, M. D., *Muscle Nerve* 22:800–822 (1999)). IgM binding to myelin-associated glycoprotein (MAG) is a marker for a demyelinating sensory-motor polyneuropathy syndrome (Nobile-Orazio, "Neuropathies associated with anti-MAG antibodies and IgM monoclonal gammopathies," in Latov, N., Wokke, J. H. J., Kell, J. J. Jr., Eds., Immunology and Infectious Diseases of the Peripheral Nerves, Cambridge, UK: Cambridge University Press, 1998: 168–189; Erb, S. et al., J. Neurol. 247:767–772 (2000)). IgM binding to sulfatide (Lopate, G., et al., *J. Neurol. Neurosurg. Psychiatry* 62:581–585 (1997); Carpo, M. et al., *J. Neurol. Sci.* 176:144–150 (2000); Erb, S. et al., *J. Neurol.* 247: 767–772 (2000)) and to β-tubulin (Connolly, A. M. et al., *Neurology* 48:243–248 (1997)) may also be associated with demyelinating sensory-motor polyneuropathies. IgM binding to GM1 ganglioside is related to a multifocal motor neuropathy that commonly has conduction block as the predominant demyelinating feature on electrophysiological testing (Parry, G., *Muscle Nerve* 19:269–276 (1996); Pestronk, A. and Choksi, R., *Neurology* 49:1289–1292 (1997); Pestronk, A., *Neurology* 51:S22–S24 (1998)). Serum IgM with selective binding to GD1b ganglioside is associated with an axonal sensory polyneuropathy and ophthalmoplegia (O'Leary, C. P. and Willison, J. J., *Curr. Opin. Neurol.* 13:583–588 (2000); Susuki, K. et al., *J. Neuroimmunol.* 112:181–187 (2001)). However, the antigenic targets of serum antibodies in approximately 40% of patients with IgM M-proteins and polyneuropathies, especially those with primary axonal involvement, have been undefined.

Because polyneuropathies are potentially treatable, correct identification of a patient's particular polyneuropathies is important. Methods of diagnosing such polyneuropathies based on specific disease-related criteria would facilitate identification of treatable disease and expedite commencement of treatment.

SUMMARY OF THE INVENTION

The current invention pertains to methods for diagnosing, in an individual, the presence or absence of a painful, predominantly sensory, polyneuropathy. The methods include assaying a test sample of bodily fluid, blood, serum or other tissue from an individual for the presence of antibodies, such as IgM antibodies, that bind to a trisulfated disaccharide sample (e.g., to a sample containing IdoA2S-GlcNs-6S). In the methods, a trisulfated disaccharide sample, which can include trisulfated disaccharide that is a component of an oligosaccharide (e.g., heparin oligosaccharide), and/or trisulfated disaccharide that is not a component of an oligosaccharide, is contacted with the test sample. The amount of antibody that binds to the tri sulfated disaccharide is then assessed and compared to a reference amount, or to the amount of anti-trisulfated disaccharide antibody in at least one negative control sample of a comparable bodily fluid or tissue. The presence of the polyneuropathy is indicated by an amount of anti-trisulfated disaccharide antibody that is greater than a reference amount, or by an amount of anti-trisulfated disaccharide antibody that is significantly greater in the test sample than in the negative control sample(s). The absence of the polyneuropathy is indicated by an amount of anti-trisulfated disaccharide antibody that is less than a reference amount, or by an amount of anti-trisulfated disaccharide antibody that is not significantly greater in the test sample than in the negative control sample(s).

The methods of the invention use disease-specific criteria to identify the presence of certain polyneuropathies, and thus allow identification of disease even in the presence of varying clinical manifestations of the disease. Identification of the particular disease allows early intervention for treatment of disease and appropriate management of disease symptoms.

BRIEF DESCRIPTION OF THE DRAWINGS

FIG. 2 is a graphic representation of titers of IgM binding to TS-HDS in different disease groups. TS-HDS: trisulfated heparin disaccharide (5 patients); MAG: IgM binding to myelin-associate glycoprotein (27 patients); AMAN: Acute motor axonal neuropathy (45 patients); GBS: Guillain-Barre syndrome (22 patients); Immune: Immune-mediated disorders without neural involvement (21 patients); ALS: Amyotrophic lateral sclerosis (21 patients); Immune: immune mediated disorders without neural involvement (21 patients); CIDP: chronic immune demyelinating polyneuropathy (24 patients); MS: Multiple sclerosis (19 patients); PN: Polyneuropathies, sensory, or sensory-motor (26 patients); HIV-PN: Painful sensory polyneuropathies in patients with HIV infection (21 patients).

Figure 1:
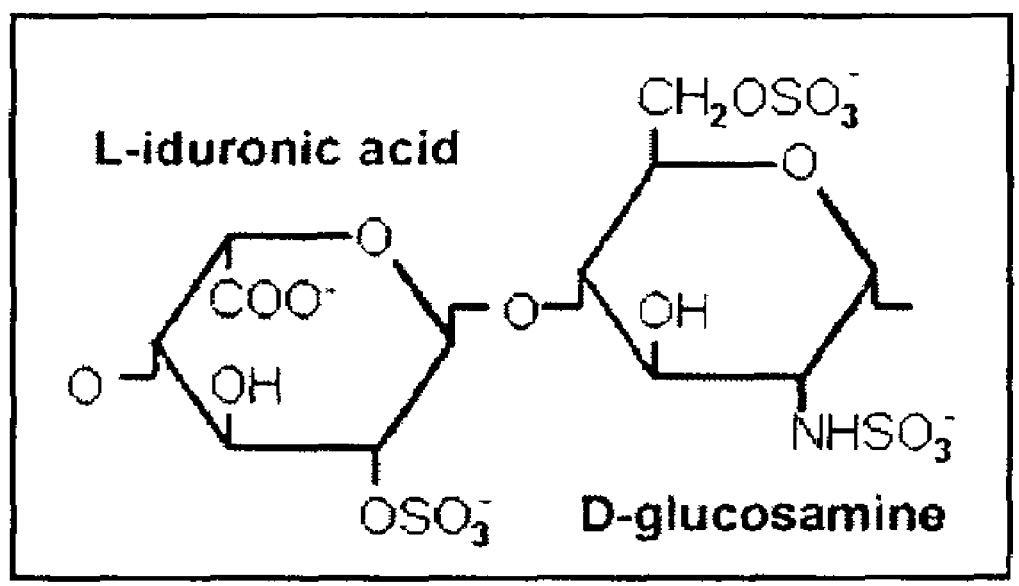
FIG. 1 is depicts a trisulfated heparin disaccharide (TS-HDS; IdoA2S-GlcNs-6S). The disaccharide is sulfated at the 2 position of the L-iduronic acid and at 2(N) and 6 positions of the D-glucosamine.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention pertains to methods for the diagnosis of a painful, predominantly sensory polyneuropathy. As described herein, the presence of IgM antibodies to a trisulfated disaccharide, IdoA2S-GlcNS-6S (TS-HDS), the most abundant component of heparin oligosaccharides, correlates with the presence of painful, predominantly sensory polyneuropathy.

As a result of this discovery, methods are now available for diagnosing painful, predominantly sensory, polyneuropathies. The methods diagnose the presence or absence of the painful, predominantly sensory, polyneuropathy in an individual, by assessing a test sample from an individual for the presence or absence of antibodies to a trisulfated disaccharide. The presence of antibodies to the trisulfated disaccharide is indicative of the presence of the painful, predominantly sensory, polyneuropathy; the absence of antibodies to trisulfate disaccharide is indicative of the absence of the painful, predominantly sensory, polyneuropathy.

In the methods of the invention, a trisulfated disaccharide sample is used. The term, "trisulfated disaccharide sample," as used herein, can be a sample containing a trisulfated disaccharide as a component of a polysaccharide (e.g., a heparin oligosaccharide comprising trisulfated disaccharide, such as IdoA2S-GlcNS-6S (TS-HDS)), or as a component of a modified protein or a peptide (e.g., as a side chain); alternatively, the trisulfated disaccharide sample can contain the trisulfated disaccharide that is not a component of another molecule. If desired, some or all of the trisulfated disaccharide in the trisulfated disaccharide sample can be modified. In a preferred embodiment, the trisulfated disaccharide sample contains heparin oligosaccharide comprising trisulfated disaccharides. In another preferred embodiment, the trisulfated disaccharide sample contains the trisulfated disaccharide, IdoA2S-GlcNS-6S (TS-HDS). In a particularly preferred embodiment, the trisulfated disaccharide sample contains IdoA2S-GlcNS-6S (TS-HDS) that is "isolated," that is, that is not a component of a polysaccharide. For example, all of the TS-HDS of the trisulfated disaccharide sample can be isolated.

The trisulfated disaccharide can be isolated from naturally-occurring sources, chemically synthesized or recombinantly produced. For example, in one embodiment, the TS-HDS can be a sample that has been isolated from heparin oligosaccharide.

The trisulfated disaccharide sample is contacted with a test sample from an individual, such as an individual who is suspected of having a polyneuropathy. The test sample can comprise blood, serum, cerebrospinal fluid, urine, nasal secretion, saliva, or any other bodily fluid or tissue. Alternatively, the test sample can comprise antibodies isolated from a sample of bodily fluid or tissue from the individual. If the sample is isolated antibodies, the isolated antibodies can include a single type of antibody (e.g., IgA, IgD, IgE, IgG or IgM antibodies), or can include all types of antibodies; alternatively, one or more types of antibodies (e.g., IgM antibodies, IgG antibodies, or IgM and IgG antibodies) can be isolated. In a preferred embodiment, the test sample is a serum sample from the individual. In another preferred embodiment, the test sample is a sample comprising IgM antibodies from the individual.

Contact of the trisulfated disaccharide sample with the test sample from the individual results in a "contacted sample," which is a mixture of trisulfated disaccharide sample and the test sample. The contacted sample is maintained under appropriate conditions to allow binding of any anti-trisulfated disaccharide antibody that may be present in the sample to the trisulfated disaccharide. The terms, "anti-trisulfated disaccharide antibody" or "anti-trisulfated disaccharide autoantibody", as used herein, refer to antibody that specifically binds to trisulfated disaccharide. An antibody that "specifically binds" to a trisulfated disaccharide, as used herein, is an antibody that preferentially binds to a trisulfated disaccharide, as compared to binding to other similar molecules (e.g., other disaccharides, other sulfated polysaccharides). The contacted sample is then assessed for the presence or absence of anti-trisulfated disacccharide antibodies.

In one embodiment of the invention, the amount of anti-trisulfated disaccharide antibodies, if any, that have bound to the trisulfated disaccharide in the contacted sample, is compared to a reference amount. The term, "reference amount," as used herein, refers to an amount of anti-trisulfated disaccharide antibodies that correlates with a diagnosis of painful, predominantly sensory polyneuropathy. A reference amount can be determined, for example, by comparing amounts of anti-trisulfated disaccharide antibodies in contacted samples from individuals known to have a painful, predominantly sensory polyneuropathy (e.g., a "positive control sample"), with amounts of anti-trisulfated disaccharide antibodies in contacted samples from individuals known not to have a painful, predominantly sensory polyneuropathy (e.g., a "negative control sample" as described below), and determining what amount of antibody correlates with disease. The reference amount can be determined by determining the amounts of antibodies in positive and/or negative control samples concurrently with determining the amount of antibodies in the contacted sample; alternatively, the reference amount can be a historically determined amount (i.e., an amount determined prior to determining the amount of antibodies in the contacted sample). For example, in one embodiment, a "reference amount" can be an amount of anti-trisulfated disaccharide antibody in the test sample that statistically is significantly greater than the amount of anti-trisulfated disaccharide antibody in comparable control sample(s), such as an amount that is at least about two standard deviations above, preferably three or more standard deviations above, and even more preferably four or more standard deviations above, the amount of anti-trisulfated disaccharide antibody in comparable control samples.

The amount of different types of antibodies (i.e., a sum including the amount of more than one type of antibody) can be compared to the reference amount; alternatively, the amount of one particular type of antibody (e.g., the amount of IgA, IgD, IgE, IgM or IgG antibody) can be compared to the reference amount. In a preferred embodiment, the antibody is IgM antibody. The reference amount is an amount of the same type of antibody as the antibody assessed in the contacted sample: for example, if the sum of the amount of different types of antibodies (i.e., including more than one type of antibody) for the contacted sample is compared to the reference amount, the sum of the amount of those types of antibodies is also used for the reference amount. If the amount of one particular type of antibody (e.g., the amount of IgM or IgG antibodies) in the contacted sample is compared with the reference amount, the amount of that type of antibodies is also used for the reference amount.

In one embodiment, the presence of an amount that is equal to, or greater than, the reference amount correlates with a diagnosis of (is indicative of the presence of) a painful, predominantly sensory polyneuropathy. An amount that is less than the reference amount correlates with (is indicative of) an absence of the painful, predominantly sensory polyneuropathy. In a preferred embodiment, the painful, predominantly sensory polyneuropathy has axonal loss, deposition of IgM in vessels and/or endoneurium, or both axonal loss and deposition of IgM.

In another embodiment of the invention, the contacted sample is assayed to determine the amount of anti-trisulfated disaccharide antibodies, if any, that have bound to the trisulfated disaccharide. The assay can determine an amount that is the sum of the amount of different types of antibodies (i.e., including more than one type of antibody); alternatively, the assay can determine the amount of one particular type of antibody (e.g., the amount of IgA, IgD, IgE, IgM or IgG antibody). In a preferred embodiment, the contacted sample is assayed to determine the amount of IgM antibody.

The amount of anti-trisulfated disaccharide antibody in the contacted sample is compared with the amount of anti-trisulfated disaccharide antibody in at least one comparable negative control sample (i.e., a sample from an individual who is not affected by a painful, predominantly sensory polyneuropathy). The negative control sample can be a sample from any individual who is not affected by a painful, predominantly sensory polyneuropathy. It is not necessary that the negative control sample be from an individual who is free of disease: for example, the negative control sample can be a sample from an individual who has another neuropathy, such as multiple sclerosis. A "comparable" negative control sample is a sample of the same type of body fluid or tissue as the test sample; alternatively, if the test sample is antibodies isolated from a sample of fluid or tissue, the comparable negative control sample is a sample of antibodies isolated from the same type of bodily fluid or tissue. More than one control sample can be used. The assay of the negative control sample determines the same type of antibody as the assay of the contacted sample: for example, if the sum of the amount of different types of antibodies (i.e., including more than one type of antibody) is detected for the contacted sample, the sum of the amount of those types of antibodies is also determined for the negative control sample. If the assay determines the amount of one particular type of antibody (e.g., the amount of IgM or IgG antibodies) in the contacted sample, the amount of that type of antibodies is also determined for the negative control sample. In a preferred embodiment, more than one control sample can be used.

The amount of antibody, or the presence or absence of antibody, can be determined by a variety of methods using standard techniques, including enzyme-linked immunosorbent assay (ELISA) or other solid phase immunoassays, radioimmunoassay, nephelometry, electrophoresis, immunofluorescence, Western blot (immunoblot), or other methods (see Ausubel, F. M. et al., eds., Current Protocols in Molecular Biology, John Wiley & Sons, including supplements through 2001, especially units 11.2 (ELISA) and 11.16 (Determination of Specific Antibody Titer)). In a preferred embodiment, the titer is determined by ELISA; in another preferred embodiment, the amount (or presence or absence) of antibody is determined by Western blot. In another preferred embodiment, the trisulfated disaccharide is attached to a solid support, in a manner that optimizes antibody binding to the epitopes, such as by use of a solid support modified to allow covalent linkage of compounds on its surface (e.g., Nunc CovaLink NH microwell ELISA plates) (see, e.g., U.S. Pat. No. 6,077,681, the entire teachings of which are incorporated herein by reference).

Typically, the amount of antibody that binds to the trisulfated disaccharide sample can be determined using a detector antibody that binds to the anti-trisulfated disaccharide antibody. Titers of anti-trisulfated disaccharide antibodies can be calculated from the amount of detector antibody bound to the anti-trisulfated disaccharide antibody, using standard conversion algorithms. For example, if the detector antibody comprises horseradish peroxidase, titers of antibody can be calculated as set forth in Pestronk et al. (*Ann. Neurol.* 27:316–326 (1990)). In one embodiment of the invention, the titer of anti-trisulfated disaccharide IgM antibodies in the test sample is compared to the titer of anti-trisulfated disaccharide IgM antibodies present in at least one comparable negative control sample.

The presence of an amount of anti-trisulfated disaccharide antibody in the test sample that is significantly greater than the amount of anti-trisulfated disaccharide antibody in a comparable control sample(s), correlates with the presence of a painful, predominantly sensory polyneuropathy. The presence of an amount of anti-trisulfated disaccharide antibody in the test sample that is not significantly greater than the amount of anti-trisulfated disaccharide antibody in a comparable control sample(s), correlates with an absence of the painful, predominantly sensory polyneuropathy.

In a preferred embodiment, an amount of anti-trisulfated disaccharide antibody in the test sample that is "significantly greater" is an amount that is at least about two standard deviations above the amount of anti-trisulfated disaccharide antibody in comparable control samples, and is preferably two or more standard deviations above; more preferably three or more standard deviations above; and even more preferably, four or more standard deviations above. For example, if the titer of both IgM and IgG antibody is measured, an amount of the combination of anti-trisulfated disaccharide IgM antibody and anti-trisulfated disaccharide IgG antibody that is equal to, or greater than, two standard deviations above the amount of the combination of anti-trisulfated disaccharide IgM antibody and anti-trisulfated disaccharide IgG antibody in comparable control samples is "significantly greater" and therefore correlates with the painful, predominantly sensory polyneuropathy. In another example, if titer is used, a titer of anti-trisulfated disaccharide antibody, particularly anti-trisulfated disaccharide IgM antibody, in the test sample that is equal to, or greater than, three standard deviations above the titer of anti-trisulfated disaccharide antibody in comparable control samples, correlates with a diagnosis of the painful, predominantly sensory polyneuropathy.

If desired, when determining the amount of anti-trisulfated disaccharide antibody, the amount of one or more control antibodies present in the sample can be subtracted from the detected amount of anti-trisulfated disaccharide antibody, in order to yield a corrected amount of anti-trisulfated disaccharide antibody. For example, in one embodiment, an amount of antibody to a control disaccharide, such as a different uronic acid-glucosamine disaccharide, can be subtracted; in another embodiment, an amount of antibody to histone H3 can be subtracted; and in yet another embodiment, the amount of antibody to the control disaccharide and the amount of antibody to histone H3, can both be subtracted.

The present invention also includes kits to be used in methods of the invention. Kits can include the following components: (1) a trisulfated disaccharide sample; and, optionally, (2) labeled detector antibody that binds to anti-body, preferably to the anti-trisulfated disaccharide antibody, and even more preferably, to anti-trisulfated disaccharide IgM antibody. Detector antibody can comprise an antibody bound to a detectable agent, such as an enzyme, radioactive molecule, or fluorescent agent. If the detector antibody is bound to an enzyme that reacts with an added substrate to yield a colored product, such as horseradish peroxidase, the kit can also include the substrate. The trisulfated disaccharide sample in the kit can be adhered to a solid support.

The following Exemplification is offered for the purpose of illustrating the present invention and are not to be construed to limit the scope of this invention. The teachings of all references cited herein are hereby incorporated by reference in their entirety.

Exemplifacation: Correlation Between Antibodies to Trisulfated Disaccharides and Polyneuropathies Methods ELISA Antibody Assays Serums were assayed, using ELISA methodology, for IgM binding to purified glycolipids, heparin and oligosaccharides (Sigma, St. Louis, Mo.). TS-HDS is α-4-deoxy-L-threo-hex-4-enopyranosyluronic acid-2S-[1->4]-D-glucosamine-S-6S (H9267; IdoA2S-GlcNS-6S, Sigma, St. Louis, Mo.). TS-HDS (see FIG. 1) contains two sugars, L-iduronic acid linked to D-glucosamine. There are two O-linked sulfates located at the 2 position on the iduronic acid and the 6 position on the D-glucosamine. The one N-linked sulfate is linked to the D-glucosamine. Nunc CovaLink NH Microwell ELISA plates (Nunc; Roskilde, Denmark) were used; these plates optimize antibody binding to carbohydrate epitopes (Pestronk, A., Neurology 51:S22–S24 (1998); Pestronk, A. et al., J. Neuroimmunol. 91:204–209 (1998)).

Glycolipids (0.15 µg), and heparins, proteoglycans and GAGs (0.5 µg) were dissolved in 50 µl of 0.05% N-hydroxysuccinamide and added to the wells of the ELISA plates. Fifty µl of 0.2% N-(3-dimethylaminopropyl-N-ethyl-carbodiimide (EDC) (Sigma) was added to the wells. ELISA plates were incubated overnight at 4° C., and washed three times with phosphate-buffered saline (PBS)-0.005% Tween 20. Remaining binding sites in all ELISA wells were blocked with 1% human serum albumin (for IgM) or 1% normal goat serum (for IgG), in PBS (100 µl) for four hours at room temperature. Plates were then washed 3 times with 1% normal goat serum in PBS. Subsequent steps were performed at 4° C. Between steps washing (×5) was performed using PBS with 1% normal goat serum without detergent. All serums were tested in duplicate by adding dilutions ($1:3\times10^3$ to $1:10^6$ in PBS with 1% normal goat serum) to wells overnight. The binding of IgM was measured using 4 hour exposure to goat anti-human IgM linked to horseradish peroxidase (HRP) (Organon Teknika-Cappel; West Chester, Pa.) in PBS with 1% BSA (1:20,000). Color was developed with 100 µl substrate buffer (0.1 M citrate buffer, pH 4.5 with 0.004% hydrogen peroxide and 0.1% phenylenediamene) for 30 minutes. Optical density (OD) was determined at 450 nm. The titer of selective serum IgM binding to TS-HDS was calculated by subtracting the levels of serum IgM binding to another uronic acid-glucosamine disaccharide (H9392; IdoA2S-GlcNS; Sigma, St. Louis, Mo.). High titers of selective IgM binding to TS-HDS (>12,000) were those more than 4 standard deviations above the means of a separate initial series of tests in serums from 10 ALS patients and 10 normals.

Serum Samples

The results of serum testing in the five patients were compared to the results in 226 disease-specific controls. The controls were obtained from patients with amyotrophic lateral sclerosis (ALS) (N=21), chronic immune demyelinating polyneuropathy (CIDP) (N=24), sensory, or sensory-motor, polyneuropathies (including 10 patients older than 60 years) (N=26), painful sensory polyneuropathies in patients with HIV infection (N=21), IgM M-proteins with binding to MAG (N=27), Guillain-Barre syndrome (N=22), acute motor axonal neuropathies (AMAN) (N=45), multiple sclerosis (N=19), and immune disorders without neural involvement (myasthenia gravis, inflammatory myopathies, and systemic lupus) (N=21).

Muscle and Nerve Morphology

Cryostat sections of rapidly frozen muscle and nerve biopsies were processed in a standard fashion (Blume, G. et al., Brain 120:39–45 (1997); Dubowitz, Muscle biopsy, A Practical Approach, London: Balliere Tindall 1985:19–40; Jacobs, J. M. and Love, S., Brain 108:897–924 (1985)). The muscle pathologist was blinded to the status of anti-TS-HDS antibodies in the serum at the time of biopsy interpretation. Immunocytochemistry was performed using standard protocols (Lopate, G. et al., J. Neurol. Sci. 188:67–72 (2001)) for IgM binding to muscle and nerve using peroxidase-conjugated antibodies to human IgM (Sigma; St. Louis, Mo.).

Patient Data

All available charts and laboratory data were reviewed for the five paitents with high titers of serum IgM binding to heparin. The patients were identified during testing of serum for evaluation of neuropathies in the neuromuscular clinical laboratory at Washington University in St. Louis.

Patient 1. A 71 year old woman developed severe burning, and occasional stabbing, sensations on the soles of both feet that progressed over a 2 year period. She stopped bowling during the second year because of difficulty with balance. On examination, cranial nerves, strength and cerebellar testing were normal. Tendon reflexes were reduced at the ankles but normal elsewhere. Sensation was decreased distally in the legs in a symmetric stocking distribution to vibration, pin, temperature and touch, but not proprioception. Serum immunofixation revealed an IgMκ M-protein. Total serum IgM was elevated at 268 mg/dl (normal 30–210 mg/dl). Motor and sensory nerve conduction studies were normal. Conduction velocities ranged from 48 to 67 m/s. A nerve biopsy showed loss of large and small myelinated axons. The degree of myelination was generally appropriate for axonal size. Regenerating clusters of small axons were present. Scattered thinly myelinated axons, usually in regenerating clusters, were present. Muscle biopsy showed only scattered small angular muscle fibers.

Patient 2. A 63-year-old woman developed fatigue, distal numbness and paresthesias, and progressive gait imbalance over 2 years. She noted intermittent falling. On examination, she had normal strength. Tendon reflexes were absent at the ankles but 2+ elsewhere. Sensation was decreased to all modalities except proprioception distally in a symmetric stocking-glove distribution. Serum immunofixation revealed no M-protein. Total IgM was elevated at 1420 mg/dl (normal 30–210 mg/dl), but levels of IgA and IgG were normal. Nerve conduction studies showed small peroneal nerve compound motor action potentials (CMAPs) and small or absent sural sensory nerve action potentials (SNAPs). Sensory and motor nerve conduction velocities were normal in the legs and arms. Muscle biopsy showed chronic and ongoing denervation with small angular fibers and a mild degree of fiber type grouping.

Patient 3. A 74-year-old man noted nocturnal cramping in his calves and tingling in his feet for a year. Four years previously he had presented with anemia and a serum IgM level of 5,400 mg/dl. He was diagnosed with Waldenstrom's macroglobulinemia. Despite treatment with courses of chlorambucil, prednisone, epoetin alfa, fludarabine, 2-chlorodeoxyadenosine, rituximab, cyclophosphamide, and plasma exchange and a splenectomy, his IgM level increased and hematocrit decreased. Muscle cramps became progressively worse, awakening him up to 3 times per night, with onset after changing position in bed and relief after walking. Tingling and hot sensations developed in the soles of both feet. On general examination a multifocal skin rash was present on the right hand and forearm, and both calves. Cranial nerves were normal except for mild bilateral sensorineural hearing loss. Strength was mildly decreased distally and symmetrically in the legs. Mild weakness of hip flexion was also noted. Tendon reflexes were 1+ at the triceps and absent elsewhere. All modalities of sensation were decreased distally up to the ankles in a symmetric stocking distribution. Serum immunofixation revealed an IgMκ M-protein. Nerve conduction studies showed an axonal sensory-motor polyneuropathy. Sural SNAPs were absent.

CMAP amplitudes were generally normal in the arms and reduced in the legs, but were absent in the peroneal nerve to the extensor digitorum brevis. Sensory and motor nerve conduction velocities were borderline in the legs and normal in the arms.

Patient 4. A 70 year old female had a 5 year history of pain, tingling and numbness in the feet that often awakened her at night. Symptoms began symmetrically in the toes and progressed proximally to involve her feet. On examination, cranial nerves, strength and cerebellar testing were normal. Tendon reflexes were reduced at the ankles, but normal elsewhere. Sensation was decreased distally to all modalities except proprioception in the legs in a symmetric stocking distribution. Serum immunofixation revealed an IgMκ M-protein. Total IgM was elevated at 671 mg/dl. Motor and sensory nerve conduction studies were normal. Quantitative sensory testing was compatible with a peripheral neuropathy showing an increased threshold for temperature sensation in the feet.

Patient 5. A 70 year old female noted paresthesias, shooting pains and numbness bilaterally in her feet. During the next year symptoms spread proximally to involve the ankles and fingertips. Gait became somewhat unsteady. On examination, cranial nerves and strength were normal. Tendon reflexes were reduced at the ankles but normal elsewhere. Sensation was decreased to all modalities except proprioception distally in the legs in a symmetric stocking distribution. Serum immunofixation revealed an IgMκ M-protein. Total IgM was normal at 137 mg/dl. Nerve conduction studies showed borderline, or reduced, CMAP amplitudes in the legs. Sural SNAPs were absent. Sensory and motor nerve conduction velocities were normal in the legs and arms. A nerve biopsy showed loss of large and small myelinated axons in a somewhat patchy distribution. Scattered thinly myelinated axons, usually in regenerating clusters, were present. Inflammatory cells were noted around the perimeter of a moderate sized epineurial blood vessel. A muscle biopsy showed only scattered small angular muscle fibers.

A summary of pertinent characteristics of these five patients is set forth in Table 1.

TABLE 1

Characteristics of Patients with IgM Binding to TS-HDS

| | Patient # | | | | |
|---|---|---|---|---|---|
| | 1 | 2 | 3 | 4 | 5 |
| Onset age | 71 | 61 | 71 | 65 | 69 |
| Sex | F | F | M | F | F |
| Weakness | None | None | Distal Legs | None | None |
| Sensory loss | Pansensory Legs Symmetric | Pansensory Hands + Legs Symmetric | Pansensory Legs Symmetric | Pansensory Legs Symmetric | Pansensory Legs Symmetric |
| Pain | Burning | Paresthesias | Cramps Paresthetic | Paresthetic | Paresthetic |
| Tendon reflexes absent or reduced | Ankles | Ankles | All | Ankles | Ankles |
| Nerve conduction studies | Normal | Axonal loss, Sensory + Motor | Axonal loss, Sensory + Motor | Normal QST: Reduced | Axonal loss, Sensory |
| IgM class TS-HDS binding (IgMκ) | IgMκ | None | IgMκ | IgMκ | IgMκ |
| Titer | 75,000 | 20,000 | 82,000 | 14,000 | 13,000 |
| Class | κ only | κ only | κ only | κ only | κ only |

QST = Quantitative sensory testing

A summary of the results of motor and sensory conduction studies in these five patients is set forth in Table 2.

TABLE 2

Motor and Sensory Conduction Studies in Patients with IgM Binding to TS-HDS

| Patient # | Nerve | NCV (m/s: Distal segment) | Distal Latency (ms) | Amplitude |
|---|---|---|---|---|
| 1 | Peroneal motor | 48 (>41) | 3.9 (<6.1) | 3.5 mV (>2 mV) |
| | Tibial motor | 52 (>41) | 4.3 (<6.1) | 14.2 mV (>3 mV) |
| | Radial sensory | 67 (>50) | 1.5 (<2.0) | 34.5 μV (>10 μV) |
| | Sural sensory | 51 (>38) | 2.8 (<3.7) | 12.3 μV (>5 μV) |

TABLE 2-continued

Motor and Sensory Conduction Studies in Patients with IgM Binding to TS-HDS

| Patient # | Nerve | NCV (m/s: Distal segment) | Distal Latency (ms) | Amplitude |
|---|---|---|---|---|
| 2 | Peroneal motor | 45 | 4.5 | 1.8 mV |
|   | Tibial motor | 46 | 3.9 | 6.1 mV |
|   | Median sensory | 56 (>44) | 2.5 (<3.4) | 36 µV (>7 µV) |
|   | Sural sensory | 44 | 3.3 | 2 µV |
| 3 | Peroneal motor | Absent | | |
|   | Ulnar motor | 53 (>50) | 3.5 (<3.6) | 11.3 mV (>6 mV) |
|   | Radial sensory | 53 | 1.8 | 20.1 µV |
|   | Sural sensory | Absent | | |
| 4 | Peroneal motor | 44 | 4.9 | 4.7 mV |
|   | Tibial motor | 43 | 5.9 | 7.5 mV |
|   | Median sensory | 47 | 3.0 | 11.9 µV |
|   | Sural sensory | 45 | 3.1 | 6.3 µV |
|   | Quantitative sensory: Increased temperature threshold | | | |
| 5 | Peroneal motor | 49 | 4.9 | 3.7 mV |
|   | Tibial motor | 42 | 4.8 | 2.5 mV |
|   | Radial sensory | 55 | 1.8 | 14.4 µV |
|   | Sural sensory | | Absent | |

Numbers in parenthesis indicate normal range

Results

Serum Antibodies

Titers of IgM binding to TS-HDS in serums from the patients described above ranged from 13,000 to 82,000. IgM binding to TS-HDS was monoclonal, consisting of κ but not λ light chains, in all 5 serums. The IgM binding was selective for TS-HDS. None of the serums had high titers of IgM binding to 6 other, closely related, heparin iduronic acid-glucosamine disaccharides with fewer than 3 sulfate groups. A summary of the IgM binding to antigens is set forth in Table 3.

TABLE 3

IgM Binding to Antigens in Patients with TS-HDS Antibodies

| Antigen | Patient # 1 | 2 | 3 | 4 | 5 |
|---|---|---|---|---|---|
| Iduronic acid-Glucosamine Disaccharides (with H, Ac or S modifications on IdoA and GlcN) | | | | | |
| IdoA-2S GlcN-S-6S (TS-HDS) | 75,000 | 20,000 | 82,000 | 14,000 | 13,000 |
| IdoA-2H GlcN-Ac-6S | 0 | 0 | 19,000 | 0 | 0 |
| IdoA-2H GlcN-S-6S | 0 | 0 | 0 | 0 | 0 |
| IdoA-2H GlcN-H-6S | 0 | 0 | 0 | 0 | 0 |
| IdoA-2H GlcN-H-6H | 0 | 0 | 0 | 0 | 0 |
| IdoA-2S GlcN-H-6S | 0 | 0 | 0 | 0 | 0 |
| IdoA-2S GlcN-H-6H | 0 | 0 | 0 | 0 | 0 |
| IdoA-2S* GlcN-S-6H | 0 | 0 | 0 | 0 | 0 |
| Neuropathy-associated antigens | | | | | |
| GM1 ganglioside | 0 | 0 | 0 | 0 | 0 |
| MAG | 0 | 0 | 0 | 0 | 0 |
| Sulfatide | 0 | 106,000 | 0 | 0 | 0 |
| GD1b | 0 | 0 | 0 | 0 | 0 |
| Heparan sulfate | 0 | 40,000 | 0 | 0 | 0 |
| Heparin | 96,000 | 19,000 | 31,000 | 5,700 | 22,000 |

IdoA = iduronic acid; GlcN = Glucosamine; S = Sulfate; Ac = Acetyl; H = Hydrogen; MAG = myelin-associated glycoprotein
*Control disaccharide Two of the 226 serums in the disease-specific control group also had high titer IgM binding to TS-HDS (see FIG. 2). Both were from patients with sensory-motor demyelinating neuropathies and serum IgM binding to MAG, a glycoprotein that contains several types of sulfated oligosaccharide groups. Serums with high titers of IgM binding to TS-HDS also showed binding to heparin.

Patient Characteristics

The clinical syndromes in the five patients with selective IgM binding to TS-HDS were similar. All had onset, beginning in the seventh or eighth decade, of symptoms and signs suggestive of a sensory neuropathy. Paresthesias or other uncomfortable sensations developed early in the course of the disease. Sensory loss, especially pain, temperature and vibration, in a distal symmetric pattern, especially in the legs, was a prominent feature. Weakness was not a major component of the syndrome. Strength was normal in four of the five patients, and was mildly reduced in the feet in the remaining patient (#3). Deep tendon reflexes were most commonly absent at the ankles but easily elicited elsewhere. Laboratory evaluations showed that four of the five patients had IgMκ M-proteins detected by immunofixation. Serums from the five patients had no IgM binding to the neuropathy-associated antigens GM1 or GD1b gangliosides, myelin associated glycoprotein or chondroitin sulfate. One serum (#2) had high titers of IgM binding to sulfatide and heparan sulfate. Other laboratory studies were unremarkable.

Electrodiagnostic or pathological studies in all 5 patients were consistent with the presence of an axonal neuropathy. Three patients had electrophysiological evidence of axonal loss with reduced or absent amplitudes of sural sensory nerve action potentials. One patient (#4) had normal nerve conduction studies, but abnormal quantitative sensory testing. Nerve condition velocities were normal in all patients. In one patient (#1), all electrophysiological studies were normal, but the nerve biopsy showed a loss of unmyelinated axons.

Pathology of Muscle and Nerve

Biopsies of both nerve (sural) and muscle (gastrocnemius) were available for evaluation in patients 1 and 5. The pathology was similar in both patients. Light microscopic and ultrastructural examination of sural nerves appeared normal for age other than showing a reduced number of unmyelinated axons and the presence of scattered clusters of thinly myelinated, probably regenerating, axons. The numbers of myelinated axons (6,100/mm2 and 4,800/mm2) fell into the broad normal limits for age (Jacobs, J. M. and Love, S., Brain 108:897–924 (1985)). Unmyelinated axons were reduced in number (11,100/mm2 and 9,300/mm2). Immunohistochemistry demonstrated focal deposits of IgMκ around the outer rim of intermediate sized perimysial and epineurial veins. Scattered endomysial capillaries also stained for IgMκ. In five controls with idiopathic axonal neuropathies, no IgM, or κ or λ light chain, staining was seen in nerves or muscles.

Discussion

The results demonstrated that a trisulfated disaccharide component of heparin, IdoA2S-GlcNS-6S (TS-HDS) is an antigenic target for monoclonal serum IgM in a subset of patients with painful, predominantly sensory axonal neuropathies. The polyneuropathies in the 5 patients with high titer monoclonal IgM binding to TS-HDS but not to MAG, had several features in common. First, all had disease onset after 60 years of age with pain or paresthesias as the main initial symptom. Second, progression of symptoms, including pain and numbness, developed very slowly over periods of years to more than a decade. The degree of disability in the patients was related mainly to pain. Third, physical examination revealed several common features. There was reduced sensation in a distal, symmetric pattern. Pain, temperature and vibration modalities were affected, but proprioception was relatively spared. Strength was largely unaffected. One patient had mild distal weakness in the feet. Tendon reflexes were reduced at the ankles in all, and more generally in one patient. Fourth, the IgM binding to TS-HDS was monoclonal, and κ type, in all patients. In four of the patients this was consistent with the detection of an IgM κ M-protein in the serum. Presumably, the level of the monoclonal antibody in patient 2 was too small to be detected by immunofixation methodology. Finally, electrophysiological and pathological studies suggested axonal loss, but no demyelination. Morphometric studies of the nerve biopsies suggest that unmyelinated axons are most prominently involved. Overall, the clinical and laboratory features in most of the patients are similar to the group of older patients with idiopathic, painful polyneuropathies but relatively minor, or no, electrophysiological changes (Periquet, M. T. et al., Neurology 53:1641–1647 (1999); Holland, N. R. et al., Neurology 48:708–711 (1997)). In this large group of patients, neuropathy-associated antibodies were uncommon, but, in some patients, the syndrome might be related to polyclonal IgM binding to sulfatide (Lopate, G. et al., J. Neurol. Neurosurg. Psychiatry 62:581–585 (1997)). The prevalence of high titers of IgM binding to TS-HDS in this group of otherwise idiopathic polyneuropathies is being further evaluated.

The clinical and laboratory features in the five patients described herein, with IgM binding to TS-HDS, distinguish them from other reported groups of chronic, predominantly sensory, neuropathies that are associated with serum IgM binding to carbohydrate antigens. In neuropathies with anti-MAG antibodies, patients have distal sensory loss, usually without pain, as well as a tremor and an ataxic gait disorder (Erb, S. et al., J. Neurol. 247:767–772 (2000); Nobile-Orazio, "Neuropathies associated with anti-MAG antibodies and IgM monoclonal gammopathies," in Latov, N., Wokke, J. H. J., Kell, J. J. Jr., Eds., Immunology and Infectious Diseases of the Peripheral Nerves, Cambridge, UK: Cambridge University Press, 1998:168–189; Erb, S. et al., J. Neurol. 247:767–772 (2000)) not found in the patients reported herein. Distal weakness in the lower extremities is common in the anti-MAG polyneuropathy, occurring in 70% of patients. Pathologically, the anti-MAG neuropathy shows prominent demyelinating features in addition to distal axonal loss. IgM is most commonly deposited on myelin-related structures (Lopate, G. et al., J. Neurol. Sci. 188: 67–72 (2001)). In neuropathies with monoclonal IgM binding to sulfatide, patients have clinical and pathological features that are similar to the anti-MAG syndrome (Lopate, G., et al., J. Neurol. Neurosurg. Psychiatry 62:581–585 (1997)). In neuropathies with IgM binding to the GALOP antigen, sulfatide in a lipid membrane configuration, patients have prominent gait ataxia and a sensory neuropathy with axonal loss, and, occasionally, demyelinating features (Pestronk, A. et al., Muscle Nerve 17:1293–1300 (1994)). Patients with IgM binding to GD1b ganglioside commonly have sensory ataxia, ophthalmoplegia and some features of demyelination (Susuki, K. et al., J. Neuroimmunol. 112: 181–187 (2001); Willison, H. J. et al., Brain 124:1968–1977 (2001)). In contrast, patients with IgM binding to TS-HDS have features distinct from these groups, including prominent neuropathic pain early in, and throughout, the disease course, absence of tremor, lack of prominent distal weakness, a predominantly axonal neuropathy with no evidence of demyelination on electrophysiological and pathological testing, and IgM deposition around moderate sized blood vessels.

A summary of the comparative features of chronic neuropathies with IgM binding to carbohydrate antigens is set forth in Table 4.

TABLE 4

Chronic Neuropathies with IgM Binding to Carbohydrate Antigens: Comparative Features

| Antigen | Prominent Signs | Neuropathy Features: Electrophysiology & Pathology |
| --- | --- | --- |
| TS-HDS | Pain & Paresthesias Sensory loss: Distal | Axon loss, especially unmyelinated IgMκ deposition around vessels |
| Myelin-associated glycoprotein | Sensory loss Gait ataxia Tremor | demyelination Distal latencies: Prolonged Myelin wide spacing |
| Sulfatide | Sensory loss Gait ataxia Tremor | Demyelination Distal latencies: Prolonged Myelin wide spacing |

TABLE 4-continued

Chronic Neuropathies with IgM Binding to Carbohydrate Antigens: Comparative Features

| Antigen | Prominent Signs | Neuropathy Features: Electrophysiology & Pathology |
| --- | --- | --- |
| GD1b ganglioside | Sensory loss Sensory ataxia Ophthalmoplegia | Axon loss Demyelination |
| GM1 ganglioside | Weakness Distal; Asymmetric Arms>Legs | Demyelination Conduction block Axon loss |

Figure 2:
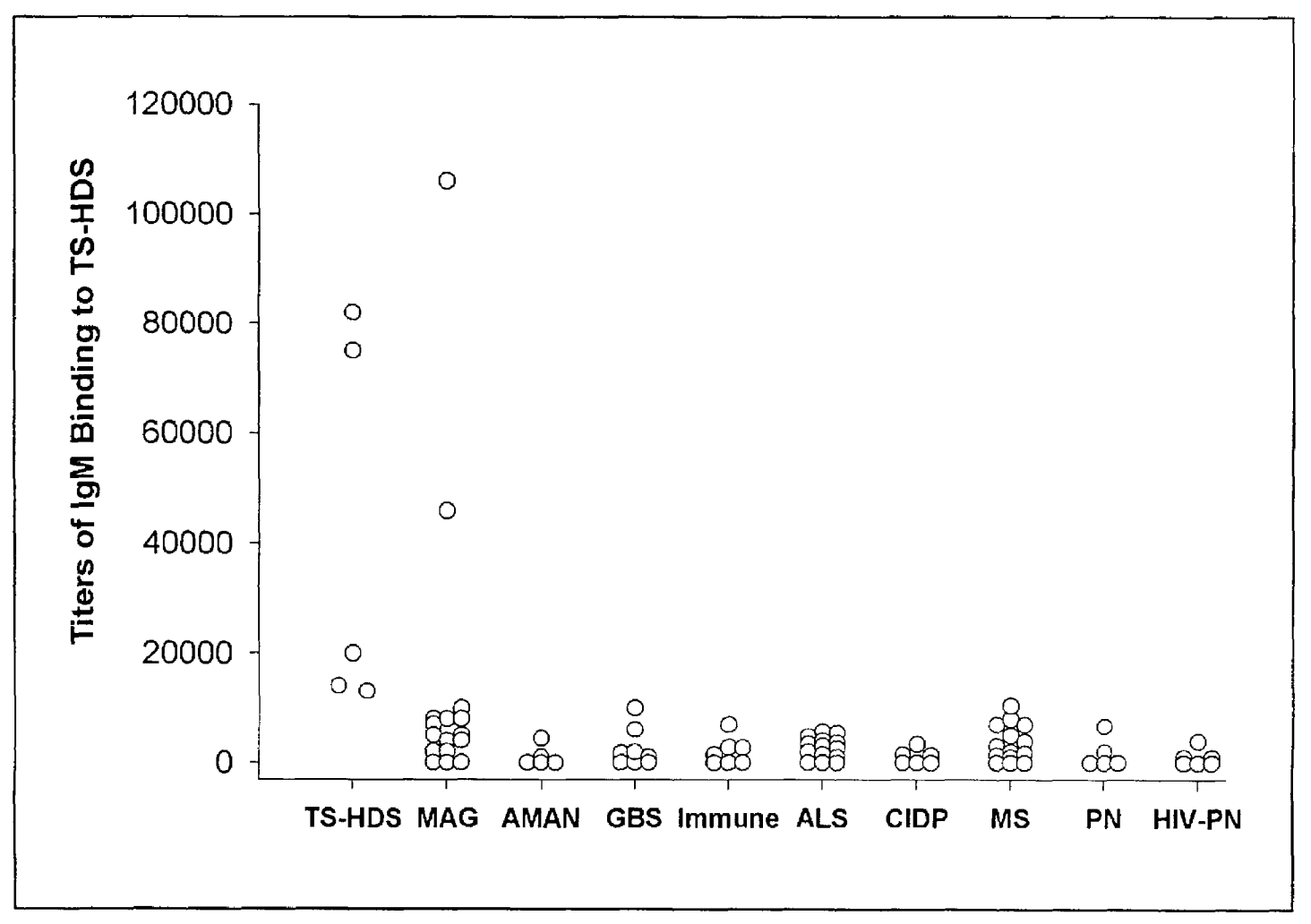

The findings herein demonstrate that IgM binding selectively to TS-HDS occurs mainly in patients with predominantly sensory, axonal neuropathy syndromes (FIG. 2). The only other group in which high titers of IgM binding to TS-HDS was found, was a subgroup of patients (7%) that also had serum IgM binding to another neuropathy-associated antigen, MAG. These patients also had a predominantly sensory neuropathy syndrome, but additionally, the neuropathy had prominent demyelinating features consistent with the presence of IgM binding to MAG, a myelin protein. The preliminary results of testing of serums from 220 unselected patients with IgM M-proteins show that binding to TS-HDS occurs in 17 (8%) and to MAG in 13 (6%).

Those skilled in the art will know, or be able to ascertain, using no more than routine experimentation, many equivalents to the specific embodiments of the invention described herein. These and all other equivalents are intended to be encompassed by the following claims.

What is claimed is:

1. A method of diagnosing the presence or absence of a painful, predominantly sensory, axonal polyneuropathy in an individual, the method comprising:
   a) contacting a trisulfated disaccharide sample comprising IdoA2S-GlcNS-6S with a test sample from the individual, wherein the test sample is selected from the group consisting of: blood, serum, cerebrospinal fluid, urine, nasal secretion, saliva, and antibodies isolated from blood, serum, cerebrospinal fluid, urine, nasal secretion, or saliva; and wherein the trisulfated disaccharide sample is contacted with the test sample under conditions that allow antibodies, if present, to bind to IdoA2S-GlcNS-6S, thereby generating a contacted sample; and
   b) comparing the amount of antibodies to IdoA2S-GlcNS-6S in the contacted sample with a reference amount of antibodies to IdoA2S-GlcNS-6S correlating with a diagnosis of painful, predominantly sensory, axonal polyneuropathy,
wherein an amount of antibodies to IdoA2S-GlcNS-6S in the contacted sample that is equal to, or greater than, the reference amount, in the absence of selective antibody binding to myelin-associated glycoprotein, is indicative of the presence of the painful, predominantly sensory, axonal polyneuropathy.

2. The method of claim 1, wherein the amount of the antibodies to IdoA2S-GlcNS-6S comprises an amount of antibodies that comprise IgM antibodies.

3. The method of claim 1, wherein the painful, predominantly sensory, axonal polyneuropathy is associated with axonal loss, deposition of IgM in vessels and endoneurium, or both axonal loss and deposition of IgM in vessels and endoneurium.

4. The method of claim 1, wherein the trisulfated disaccharide sample comprises heparin oligosaccharide.

5. A method of diagnosing the presence or absence of a painful, predominantly sensory, axonal polyneuropathy in an individual, the method comprising:
   a) contacting a trisulfated disaccharide sample comprising IdoA2S-GlcNS-6S with a test sample from the individual, wherein the test sample is selected from the group consisting of: blood, serum, cerebrospinal fluid, urine, nasal secretion, saliva, and antibodies isolated from blood, serum, cerebrospinal fluid, urine, nasal secretion, or saliva; and wherein the trisulfated disaccharide sample is contacted with the test sample under conditions that allow antibodies, if present, to bind to IdoA2S-GlcNS-6S, thereby generating a contacted sample; and
   b) comparing the amount of antibodies to IdoA2S-GlcNS-6S in the contacted sample with a reference amount of antibodies to IdoA2S-GlcNS-6S correlating with a diagnosis of painful, predominantly sensory, axonal polyneuropathy,
wherein an amount of antibodies to IdoA2S-GlcNS-6S in the contacted sample that is less than the reference amount, in the absence of selective antibody binding to myelin-associated glycoprotein, is indicative of the absence of the painful, predominantly sensory, axonal polyneuropathy.

6. The method of claim 5, wherein the amount of the antibodies to IdoA2S-GlcNS-6S comprises an amount of antibodies that comprise IgM antibodies.

7. The method of claim 5, wherein the painful, predominantly sensory, axonal polyneuropathy is associated with axonal loss, deposition of IgM in vessels and endoneurium, or both axonal loss and deposition of IgM in vessels and endoneurium.

8. The method of claim 5, wherein the trisulfated disaccharide sample comprises heparin oligosaccharide.

9. A method of diagnosing the presence or absence of a painful, predominantly sensory, axonal polyneuropathy in an individual, the method comprising:
   a) contacting a trisulfated disaccharide sample comprising IdoA2S-GlcNS-6S with a test sample from the individual, wherein the test sample is selected from the group consisting of: blood, serum, cerebrospinal fluid, urine, nasal secretion, saliva, and antibodies isolated from blood, serum, cerebrospinal fluid, urine, nasal secretion, or saliva; and wherein the trisulfated disaccharide sample is contacted with the test sample under conditions that allow antibodies, if present, to bind to IdoA2S-GlcNS-6S, thereby generating a contacted sample;
   b) determining the amount of antibodies to IdoA2S-GlcNS-6S in the contacted sample; and
   c) comparing the amount of antibodies to IdoA2S-GlcNS-6S in the contacted sample with the amount of antibodies to IdoA2S-GlcNS-6S in at least one comparable negative control sample,
wherein an amount of antibodies to IdoA2S-GlcNS-6S in the contacted sample that is significantly greater than an amount of antibodies to IdoA2S-GlcNS-6S in a comparable negative control sample, in the absence of selective antibody binding to myelin-associated glycoprotein, is indicative of the presence of the painful, predominantly sensory, axonal polyneuropathy.

10. The method of claim 9, wherein determining the amount of the antibodies to IdoA2S-GlcNS-6S comprises determining the amount of antibodies that comprise IgM antibodies.

11. The method of claim 9, wherein the amount of antibodies to IdoA2S-GlcNS-6S is determined by enzyme-linked immunosorbent assay.

12. The method of claim 9, wherein an amount of antibodies to IdoA2S-GlcNS-6S in the contacted sample that is significantly greater than an amount of antibodies to IdoA2S-GlcNS-6S in a comparable negative control sample, is an amount that is at least about three standard deviations above an amount of antibodies to IdoA2S-GlcNS-6S in comparable control samples.

13. The method of claim 9, wherein the antibodies to IdoA2S-GlcNS-6S are IgM antibodies.

14. The method of claim 9, wherein the trisulfated disaccharide sample comprises heparin oligosaccharide.

15. A method of diagnosing the presence or absence of a painful, predominantly sensory, axonal polyneuropathy in an individual, the method comprising:
   a) contacting a trisulfated disaccharide sample comprising IdoA2S-GlcNS-6S with a test sample from the individual, wherein the test sample is selected from the group consisting of: blood, serum, cerebrospinal fluid, urine, nasal secretion, saliva, and antibodies isolated from blood, serum, cerebrospinal fluid, urine, nasal secretion, or saliva; and wherein the trisulfated disaccharide sample is contacted with the test sample under conditions that allow antibodies, if present, to bind to IdoA2S-GlcNS-6S, thereby generating a contacted sample;
   b) determining the amount of antibodies to IdoA2S-GlcNS-6S in the contacted sample; and
   c) comparing the amount of antibodies to IdoA2S-GlcNS-6S in the contacted sample with the amount of antibodies to IdoA2S-GlcNS-6S in at least one comparable negative control sample,
wherein an amount of antibodies to IdoA2S-GlcNS-6S in the contacted sample that is not significantly greater than an amount of antibodies to IdoA2S-GlcNS-6S in a comparable negative control sample, in the absence of selective antibody binding to myelin-associated glycoprotein, is indicative of the absence of the painful, predominantly sensory, axonal polyneuropathy.

16. The method of claim 15, wherein determining the amount of the antibodies to IdoA2S-GlcNS-6S comprises determining the amount of antibodies that comprise IgM antibodies.

17. The method of claim 15, wherein the amount of antibodies to IdoA2S-GlcNS-6S is determined by enzyme-linked immunosorbent assay.

18. The method of claim 15, wherein an amount of antibodies to IdoA2S-GlcNS-6S in the contacted sample that is not significantly greater than an amount of antibodies to IdoA2S-GlcNS-6S in a comparable negative control sample, is an amount that is less than about three standard deviations above an amount of antibodies to IdoA2S-GlcNS-6S in comparable control samples.

19. The method of claim 15, wherein the antibodies to IdoA2S-GlcNS-6S are IgM antibodies.

20. The method of claim 15, wherein the trisulfated disaccharide sample comprises heparin oligosaccharide.

21. The method of claim 1, wherein the test sample is serum or cerebrospinal fluid.

22. The method of claim 5, wherein the test sample is serum or cerebrospinal fluid.

23. The method of claim 9, wherein the test sample is serum or cerebrospinal fluid.

24. The method of claim 15, wherein the test sample is serum or cerebrospinal fluid.

* * * * *